United States Patent [19]

Reis et al.

[11] Patent Number: 5,002,386
[45] Date of Patent: Mar. 26, 1991

[54] DEVICE FOR DIRECTING A LASER BEAM BY MEANS OF MIRROR REFLECTION IN A SLIT LAMP APPARATUS

[75] Inventors: Werner Reis, Munich; Adolf Triller, Lochham, both of Fed. Rep. of Germany

[73] Assignee: G. Rodenstock Instrumente GmbH, Munich, Fed. Rep. of Germany

[21] Appl. No.: 474,242

[22] Filed: Feb. 5, 1990

Related U.S. Application Data

[63] Continuation of Ser. No. 133,066, Nov. 12, 1987, abandoned.

[30] Foreign Application Priority Data

Mar. 12, 1986 [DE] Fed. Rep. of Germany ....... 3608287

[51] Int. Cl.$^5$ ............................................. A61B 3/10
[52] U.S. Cl. ..................................... 351/214; 351/221
[58] Field of Search ....................... 351/205, 214, 221; 128/303.1, 395

[56] References Cited

U.S. PATENT DOCUMENTS 4,541,697 9/1985 Remingan ........................ 351/205
4,772,116 9/1988 Schröder et al. ................. 351/214

FOREIGN PATENT DOCUMENTS 2464704 3/1981 France .

Primary Examiner—Paul M. Dzierzynski
Attorney, Agent, or Firm—Antonelli, Terry, Stout & Kraus

[57] ABSTRACT

A device for directing a laser beam in the path of a beam from a slit lamp of a slit lamp apparatus to an eye to be treated or examined. The device includes a slit lamp apparatus having an optical axis along which light of the slit lamp is guided, an optical system for directing a laser beam from a side opposite to the slit lamp apparatus along the optical axis of the slit lamp apparatus, and a deflector for deflecting the laser beam and the light from the slit lamp apparatus by an angle of about 90 degrees so that the laser beam and the light of the slit lamp apparatus are coaxially directed to the eye to be treated or examined.

9 Claims, 1 Drawing Sheet

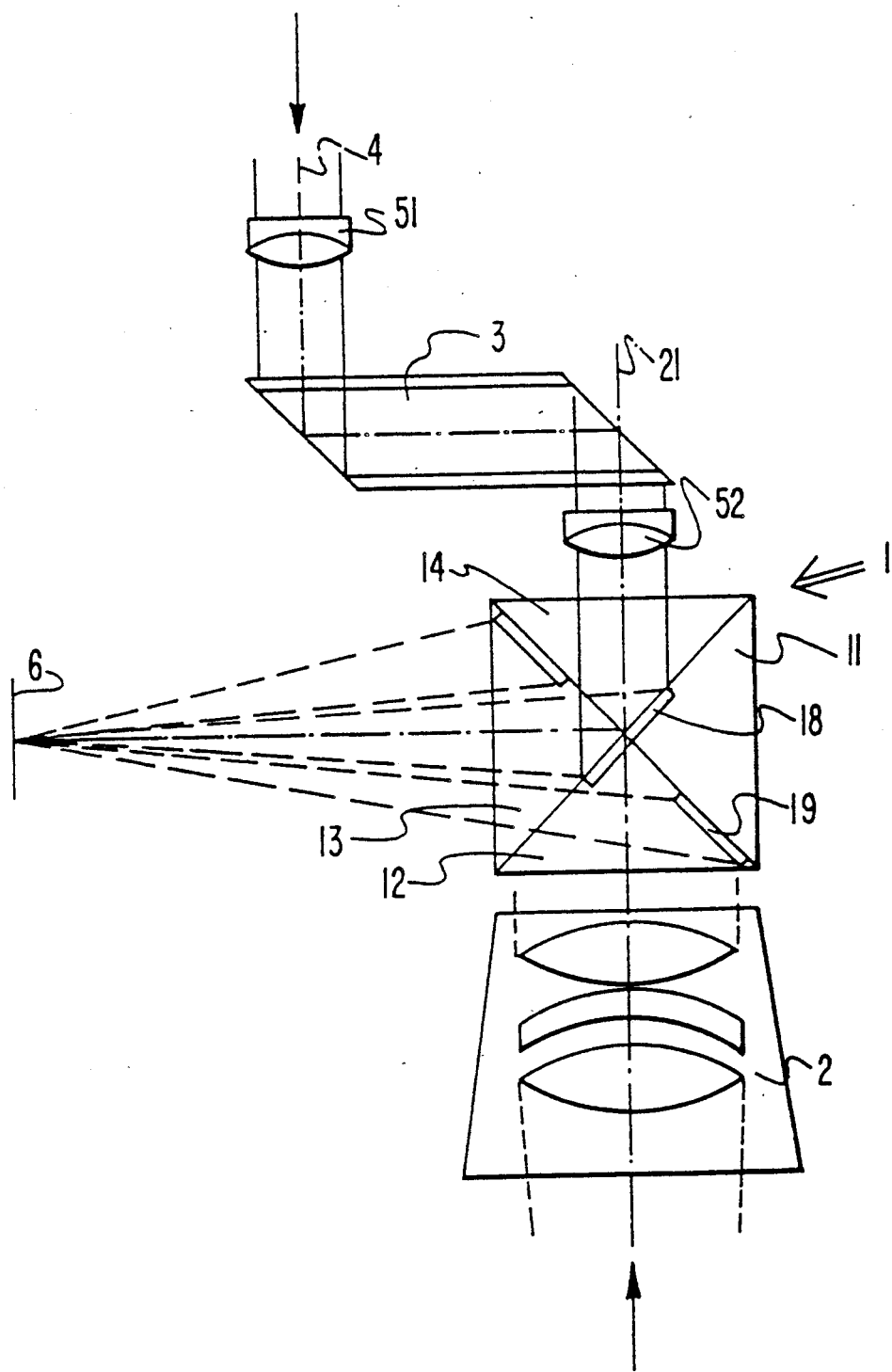

DEVICE FOR DIRECTING A LASER BEAM BY MEANS OF MIRROR REFLECTION IN A SLIT LAMP APPARATUS

This application is a continuation of application Ser. No. 133,066, filed on Nov. 12, 1987, now abandoned.

BACKGROUND OF THE INVENTION

The present invention relates to a device for directing a laser beam by means of mirror reflection in a slit lamp apparatus.

STATE OF THE ART

Such a device is known, by way of illustration, from the German Utility Model 72 25 429. In said device the laser beam is led into the encasement of the slit lamp and directed through the slit lamp to the eye to be treated or examined. Said device thus requires modifying the slit lamp, so that, by way of illustration, a laser can not be readily retrofitted to a slit lamp apparatus already at hand. Furthermore, optically it is complicated to lead both a laser beam and the light of a slit lamp, whose wavelengths may differ greatly, through the same component. Moreover, it is practically impossible to arrange elements in the path of the beam from the slit lamp, which selectively influence the laser beam, by way of illustration widening it.

For this reason, it is suggested in German Utility Model 79 25 899 to arrange, in the beam angle after the deflection prism of the lamp an additional small prism deflecting the laser beam to the eye to be examined or treated.

Although said device does not require modifying the slit lamp, it has, however, the drawback that the laser beam and the light from the slit lamp are not directed coaxially. For this reason, pivoting and rotating movements, by way of illustration, by means of a so-called micromanipulator, effect the prism deflecting the laser beam and the prism deflecting the light from the slit lamp to the eye differently.

Therefore, it has been, slit, suggested to guide the laser beam to the eye independently of the slit lamp, by way of illustration, by means of a slit lamp microscope (international patent application DE 84/00179) or by means of a separate. independently moving bunching prism. Said arrangement, however, has the disadvantage that manipulations on the slit lamp may cause the area lit by the slit lamp to no longer completely coincide with the target area of the laser.

PRESENTATION OF THE INVENTION

The object of the present invention is to provide a device to direct a laser beam by means of mirror reflection in a slit lamp apparatus, in which no lateral drifting of the laser beam from the slit lamp lighting occurs when the laser impact area is manipulated and which requires no modification of the actual slit lamp.

Surprisingly, one solution to the object of the present invention is successful, being based on directing the laser beam by means of mirror reflection and said device being improved by having the deflection element mounted on the slit lamp consist of two parts, one of which deflecting the light from the slit lamp in the known manner to the eye to be examined or treated and the other deflecting the laser beam coming from the opposite side. Accordingly the path of the laser beam runs in the elongated optical axis of the slit lamp before reaching the deflection element. As the optical axis of the slit lamp or its elongation is used jointly as the path for both beams, the laser impact area does not drift from the slit lamp light when the laser impact area is manipulated. Thus, it is possible to employ micromanipulators like the ones used in the known slit lamp apparatuses without any modifications.

The fundamental inventive idea can, of course, be employed for slit lamp apparatuses where the patient is sitting and the optical axis of the slit lamp runs vertically. Likewise, it is also possible to use the fundamental inventive idea for slit lamp apparatuses where the patient is lying and the optical axis of the slit lamp first runs horizonitally.

The deflection element deflecting the two paths of the beams from the slit lamp and from the laser heading toward each other to the eye to be treated or examined may, by way of illustration, consist of two plain mirrors. It is particularly advantageous, however, when the deflection element is designed as a divider cube composed of four identical prisms. The interface areas of the prisms are at least partially mirror coated in such a manner that beams from the slit lamp and the laser beam entering from opposite sides of the divider cube are deflected 90 degrees to the eye.

In order to reduce reflection, losses it is advantageous if the four prisms forming the divider cube are cemented to each other.

The mirror coating of the individual prims can be of such manner that the laser beam runs in the beam path to the slit lamp.

Furthermore, it is also possible to coat the prisms or mirrors wavelength selectively if the wavelengths of the laser and of the light from the slit lamp differ substantially.

In any case, it is, however, possible to influence the cross-section of the laser beam as desired. By way of illustration, beam bending elements may be provided before the deflection element, which are homed in on in such a manner that the laser beam "scans" a specific pattern, by way of illustration a large coagulation area or a cut to be executed on the cornea.

According to a feature of the present invention the path of the laser beam is first run set off from the optical axis of the slit lamp and deflected into the elongated optical axis of the slit lamp by an offset prism situated just before the deflection element. This arrangement has the advantage that the area between the optical axis of the path of the laser beam and the slit lamp microscope is increased in such a manner that, by way of illustration, an argon laser can be directly mounted on the slit lamp.

In any case, the invented device, has, however, the advantage that by directing the laser beam and the slit lamp light by means of mirror reflection in the same axis yet from opposite sides there is no relative shifting between the laser impact area and the path of the light beam. In this manner, the invented device permits employing the known micromanipulators to influence the point of impact of the laser beam.

Moreover, measures for influencing the cross-section of the beam, such as use of vario-optics of an eccentric element to scan a large area (patent application P 35 32 464.3) may be employed without hesitation.

In addition, the invented device is suitable for apparatuses provided with a target and treatment beam, by way of illustration for neodymium YAG lasers with a helium neon m, for excimer lasers.

BRIEF DESCRIPTION OF THE DRAWING

The present invention is made more apparent in connection with a preferred embodiment with reference to the drawing, whose sole figure depicts a cross-section of an invented device.

A PREFERRED EMBODIMENT OF THE INVENTION

The invented device is provided with a deflection element 1 mounted on a slit lamp 2. In the preferred embodiment depicted in the drawing hereto, the deflection element 1 is a divider cube composed of four identical prisms 11, 12, 13 and 14. On the side opposite the slip lamp is another prism 3, which deflects the path 4 of the beam of a laser, which is not shown, by way of illustration an argon laser, in such a manner that it enters the elongated optical axis 21 of slit lamp 2, but from the opposite side of divider cube 1. In the path 4 of the laser beam are also beam-influencing elements 51 and 52 provided, whereby element 52, which is an achromatic lens, is cemented to the exit surface of the second prism 3. Element 52 focusses the laser beam on the eye 6 to be treated or examined.

The interfaces of prisms 11 to 14 forming the divider cube 1 have mirror coatings 18 and 19 vaporized onto them, whereby the "inner" mirror surface 18 deflects the laser light and the ring-shaped mirror coating 19 the slit lamp light to the eye 6 in such a manner that the laser light runs "within" the slit lamp light.

The device illustrated in the figure has a number of advantages:

By means of the joint optical axis 21 of the laser light and the slit lamp light, manipulating the laser impact area does not cause the laser beam to drift laterally from the slit lamp light. In this manner it is possible to move the divider cube 1 and the prism 3 with the cemented on focussing achromatic lens jointly by means of a prior art micromanipulator.

Moreover, by means of the joint divider cube, arranged in the elongated optical axis of the slit lamp, for the laser light and the slit lamp light, the observer, by way of illustration, observing the operation through the slit lamp microscope, sees no vignetting.

By means of the deflection prism 3, offsetting the axis of the laser beam from the axis of the slit lamp, the area in the direction toward the slit lamp is increased in such a manner that, by way of illustration, an argon laser can be mounted directly.

The present invention has been made more apparent in the preceeding in connection with the preferred embodiment, but a great number of different modifications are, of course, possible within the general scope of the inventive idea:

Thus it is possible to substitute a different optical element for the divider cube deflecting the light from the slit lamp and the light from the laser beam, entering from the opposite side, to the eye. Furthermore, the mirror coatings 18 and 19, on the prisms 11 to 14 forming divider cube 1, may also be replaced by wavelength selective coatings.

Naturally, it is also possible to employ other lasers instead of the argon laser used in the preferred embodiment, by way of illustration an excimer laser, a neodymium YAG laser or a laser with a wavelength of 3<m. With these lasers, a target laser can also be employed additionally without difficulty.

In any case, the invented device has the advantage that, contrary to the prior art devices, in which the light is directed through the slit lamp, any desired number of beam influencing elements can be provided before deflecting the laser beam, by way of illustration, which can alter the size of the area by means of scanning or vario-optics, whereby, in particular, a "scanning device" as described in the German patent application 35 32 464.3 can be used.

What I claim is:

1. A device for directing a laser beam in the path of a beam from a slit lamp of a slit lamp comprising a slit lamp apparatus having an optical axis along which light of the slip lamp is guided, means for directing a laser beam from a side opposite to the slit lamp apparatus along the optical axis of the slit lamp apparatus, and deflection means for deflecting the laser beam and the light from the slip lamp apparatus by an angle of about 90 degrees so that the laser beam and the light of the slip lamp apparatus are coaxially directed to the eye to be treated or examined, the laser beam directing means directing the laser beam along the optical axis of the slit lamp apparatus prior to deflection of the laser beam by the deflection means, wherein the deflection means includes a divider cube having four identical prisms with two mirror surfaces intersecting each other at an angle of 90 degrees, one of the mirror surfaces deflecting the light from the slit lamp apparatus and the other of the mirror surfaces deflecting the laser beam so that the impingement of the laser beam on the eye to be treated or examined is maintained within the impingement area of the light from the slit lamp apparatus on the eye to be treated or examined independent of movement of the device.

2. A device according to claim 1, wherein the divider cube having four identical prisms have interface surfaces at least partially coated with a reflective coating.

3. A device according to claim 2, wherein the four prisms are cemented to each other.

4. A device according to claim 3, wherein respective ones of the prisms are coated with the reflective coating so that the laser beam is guided within a path of the light from the slit lamp apparatus.

5. A device according to claim 2, wherein the respective prisms have a wavelength selective reflective coating.

6. A device according to claim 1, wherein the laser beam directing means includes means for guiding the laser beam from a path offset with respect to the optical axis of the slit lamp apparatus onto a path along the optical axis of the slit lamp apparatus.

7. A device according to claim 6, wherein the guiding means includes mirror members.

8. A device according to claim 6, wherein the guide means includes a setoff prism.

9. A device according to claim 8, wherein an optical focusing element is provided between the setoff prism and the deflecting means.

* * * * *